United States Patent [19]
Zierenberg et al.

[11] Patent Number: 5,645,050
[45] Date of Patent: Jul. 8, 1997

[54] POWDER INHALER WITH POWDER CARRIER CONSISTING OF REGULAR MICROSTRUCTURES

[75] Inventors: Bernd Zierenberg; Dieter Hochrainer, both of Bingen, Germany

[73] Assignee: Boehringer Ingelheim KG, Ingelheim am Rhein, Germany

[21] Appl. No.: 244,879

[22] PCT Filed: Dec. 11, 1992

[86] PCT No.: PCT/EP92/02867
§ 371 Date: Aug. 10, 1994
§ 102(e) Date: Aug. 10, 1994

[87] PCT Pub. No.: WO93/12831
PCT Pub. Date: Jul. 8, 1993

[30] Foreign Application Priority Data

Dec. 20, 1991 [DE] Germany .................. 41 42 238.4

[51] Int. Cl.[6] .................................................. A61M 15/00
[52] U.S. Cl. ..................... 128/203.15; 128/203.12; 128/203.21; 128/200.22; 604/58
[58] Field of Search ................ 128/203.15, 203.21, 128/200.22, 203.12, 200.17; 604/58, 68, 69, 71

[56] References Cited

U.S. PATENT DOCUMENTS

| | | | |
|---|---|---|---|
| 2,816,549 | 12/1957 | Webster | 128/203.15 |
| 3,967,761 | 7/1976 | Melton, Jr. et al. | 128/203.15 |
| 3,998,226 | 12/1976 | Harris | 128/203.15 |
| 4,735,358 | 4/1988 | Morita et al. | 239/1 |
| 5,039,561 | 8/1991 | Debe | 427/255.6 |
| 5,192,548 | 3/1993 | Velasquez et al. | 128/203.12 |
| 5,204,113 | 4/1993 | Hartley et al. | 424/45 |
| 5,347,999 | 9/1994 | Poss et al. | 128/203.21 |
| 5,349,947 | 9/1994 | Newhouse et al. | 128/203.21 |
| 5,388,573 | 2/1995 | Mulhauser et al. | 128/203.15 |

FOREIGN PATENT DOCUMENTS

| | | | |
|---|---|---|---|
| 5558890 | 11/1990 | Australia | 604/58 |
| 2129691 | 5/1984 | United Kingdom | 128/203.15 |
| 9013328 | 11/1990 | WIPO | |
| 9200115 | 1/1992 | WIPO | |
| 2004066 | 3/1992 | WIPO | 128/203.15 |
| 9204066 | 3/1992 | WIPO | 604/58 |

*Primary Examiner*—V. Millin
*Assistant Examiner*—V. Srivastava
*Attorney, Agent, or Firm*—Robert P. Raymond; Wendy E. Rieder; Alan R. Stempel

[57] ABSTRACT

In an inhaler for powdered drugs, flat carriers are used which have regular microstructures between which the powder for inhalation is embedded.

8 Claims, 2 Drawing Sheets

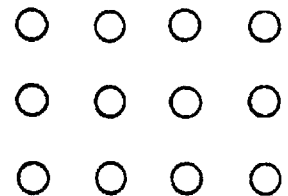
FIG.3a.
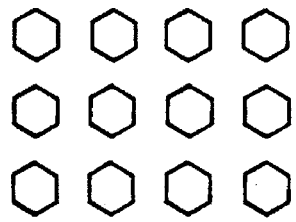
FIG.3b.
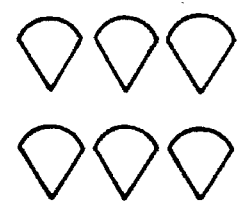
FIG.3c.
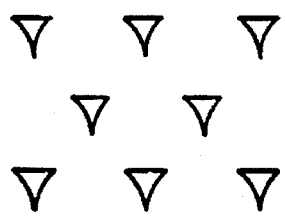
FIG.3d.
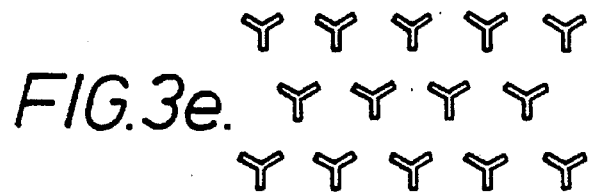
FIG.3e.
FIG.3f.

POWDER INHALER WITH POWDER CARRIER CONSISTING OF REGULAR MICROSTRUCTURES

BACKGROUND OF THE INVENTION

1. Field of the Invention

The invention relates to powder inhalers in which the powder used for inhalation is placed in readiness on carriers having specific regular microstructures.

2. Background Art

Of the numerous types of devices for powder inhalation which have already been described, there are some with belt-shaped carriers (WO 90/13328). Such carriers may have very different surface structures, e.g. conical depressions stamped into plastics film for holding the powder, or they may consist, for example, of woven or non-woven (fleece-like) fibrous material in which the powder is incorporated between the fibres or in gaps in the fabric.

SUMMARY OF THE INVENTION

As has now been found, it is particularly favourable to use microstructures arranged in a regular configuration on the carrier surface for the storage and delivery of the powder for inhalation.

DESCRIPTION OF THE PREFERRED EMBODIMENTS

The microstructures are individual elevations on the planar, belt or plate, or disc-shaped carriers. The microstructures may take various forms, e.g. they may be cylindrical, bump-like, prismatic, conical or frustoconical, they may be in the form of strips or ribs or pyramids or truncated pyramids. The axis directed towards the carrier is preferably perpendicular thereto but it may also form an angle of <90° therewith. The cross-section of the microstructures may be constant, in accordance with what has been said above, but may also vary in form and surface area as the distance from the carrier increases. The cross-section is preferably circular or elliptical or is a regular polygon. However, it may also be of irregular shape, e.g. an irregular polygon or a combination of round and angular shapes, Y- or cross-shaped or lenticular.

The height of the microstructures may be between about 10 and 500 µm, the range from 50 to 200 µm being preferred. The diameter or the corresponding lateral spacings, in the case of a non-circular cross-section, is between about 10 and 500 µm, preferably 30 to 100 µm.

It has proved favourable for the spacing between the microstructures to range from about 10 to 500 µm and more particularly from about 30 to 100 µm.

The surfaces are usually very smooth (optically reflective) and the peak-to-valley height is about 50 nm. However, a significantly greater degree of roughness is also possible for the purpose intended. For example, the peak-to-valley height in microstructures produced with the aid of etching processes is of the order of 10 µm.

The porosity is the ratio of free volume between the microstructures to the total volume filled with microstructures. In the case of prismatic or cylindrical structures, this is equal to the ratio of the surface not covered by microstructures to the total surface area.

The porosity may be adjusted within wide limits, e.g. in the range from 10 to 98% by a suitable choice of forms, sizes and spacings of the microstructures. Typical values are in the range from 50 to 80%. The choice of the figure will also depend on the nature and dosage size of the drug used. As a rule, for particularly small dosages, it is preferable to use a carrier which has a higher density of microstructures, i.e. a lower porosity.

The carriers used according to the invention are preferably produced by injection moulding. Accordingly, the materials generally used are those which can be worked by this process, such as polymethacrylate, polyamide and polyoxymethylene.

The charging of the microstructures with powder can be carried out, for example, by applying powder to the microstructures and using a doctor blade both to press the powder into the microstructures and to wipe off any excess. Another possibility is to fill the microstructures with the powder using a fine brush or other kind of brush. It has proved particularly useful to press the microstructures into the powder so that the powder penetrates into the interstices and a lightly compacted layer adhering to the surface is then removed by means of a blade. The adhesion of the powder between the microstructures is so good that the powder is not flung out of the microstructures even at acceleration forces of some tens of thousands of meters/second$^2$ (=several thousand g).

The load per unit of area is obtained essentially from the porosity, the height of the microstructures and the density of the powder applied. In the case of a conventional broncholytic such as Fenoterol the density is about 600 kg/m$^3$. The load is between 0.3 and 10 mg/cm$^2$, typical values being between 4 and 6 mg/cm$^2$.

The dosage is obtained from the load and the surface area blown, the blown area being between about 4 and 50 mm$^2$. This results in dosages of between about 0.012 and 5 mg. Typical values are between 0.05 and 0.5 mg. With inhalation devices of different configurations it is also possible for substantially larger areas to be blown, although it is not generally necessary to use more than 100 mm$^2$ per single dose.

There are carriers with a structured surface for powdered drugs in which the structures consist of small depressions (hollows) (e.g. according to EP-A-0455 463). The depressions are filled with the drug. The depressions are separated by strips which form the walls of the depressions. By contrast, the space in which the columnar microstructures are located in this application according to the invention is cohesive. This means that when the powder is blown out of these microstructures a target surface for the air current is formed. As a result (I) the powder can be blown out of the columnar microstructures leaving virtually no residue (whereas, in the case of, for example, hollow-shaped structures with a depth of 45 µm a residue of 65% of the drug is left behind in the hollows) and (II) on the other hand the dispersal is substantially better than it is with surfaces structured with hollows. Thus, when using micronised Fenoterol with an air blast of 5 cm$^3$ and 1 bar of overpressure, a lung-directed proportion of >50% was achieved in the aerosol produced (particle size <6 µm) whereas the lung-directed proportion in an aerosol from surfaces structured with hollows is only 5 to 15%.

The non-lung directed proportion of an aerosol is deposited predominantly on the walls of the oral and pharyngeal space and absorbed or swallowed. The substantially greater inhalable proportion compared with other powder nebulisers is particularly advantageous for drugs having systemic side effects. These are all the weaker, the less drug enters the body outside the target organ, assuming the same therapeutic dose.

Belt-shaped carriers according to the invention may be used in inhalation devices as known from the prior art, e.g. from the above-mentioned Application WO 90/13328. The new powder carriers may also be wrapped in a known manner, e.g. with aluminium foil which is only removed just before use.

It has proved particularly convenient in practice to use rigid or stiff carriers in the form of elongated strips or, in particular, in the form of circular discs.

Carriers of this kind can be manufactured using the so-called LIGA technology [E. W. Becker, W. Ehrenfeld, P. Hagemann, A. Maner, D. Münchmeyer: Herstellung von Mikrostrukturen mit großem Aspektverhältnis und großer Strukturhöhe dutch Röntgentiefenlithografie mit Synchrotronstrahlung, Galvanoformung und Kunststoffabformung (LIGA process), Microelectronic Engineering 4 (1986), 35–56]. In this process, first a mask of the desired structure is produced, which is impervious to synchrotron radiation. A resist which is sensitive to synchrotron radiation is irradiated through this mask. In the next stage of the development the irradiated sections are removed from the resist and filled with metal during the subsequent galvanomoulding process. Then the remaining resist is removed from the metal structure. Finally, this metal structure is used as the mould for a special injection moulding process.

Good results are also achieved with microstructures produced by conventional injection moulding. The preferred forms are plates or belts provided with ribs or cup-shaped (knob-like) elevations. The mould for injection moulding may in these cases be produced by etching a steel tool, the pattern of the structures being provided by projecting a corresponding design onto a photoresist.

In addition to the geometric properties of the microstructures, chemical-physical material properties also play a part within the scope of the invention. For the active substance Fenoterol hydrobromide, for example, a polypropylene (Novolen®) has proved particularly suitable for the adhesion. However, it is generally possible to use plastics of all kinds, such as polyamides (e.g. Vestamid®, Zytel®), polycarbonates (e.g. Makrolon®), acrylonitrile/butadiene/styrene polymers (Terluran®). If desired, the person skilled in the art will be able to determine, by simple tests, the microstructures and material properties which are most suitable for this purpose, e.g. if it is important to achieve particularly good adhesion of the powder to the carrier or, conversely, to facilitate the release from the mould.

BRIEF DESCRIPTION OF THE DRAWINGS

Understanding of the present invention and the various aspects thereof will be facilitated by reference to the accompanying figures, submitted for purposes of illustration only and not intended to define the scope of the invention.

A powder inhaler in which circular discs are used as the carrier is shown in FIG. 1. FIGS. 3a to 3f show examples of the microstructures according to the invention.

Figure 1:
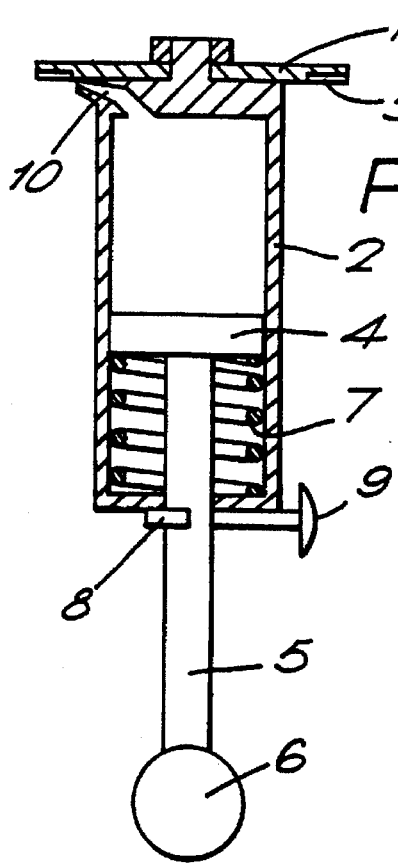
Figure 2:
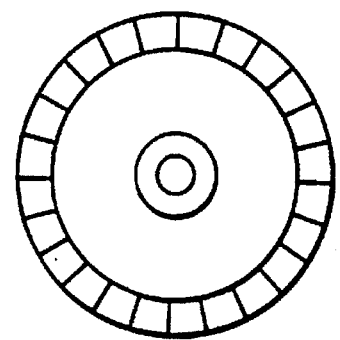
FIGS. 2 to 2b show carriers which fit it.
Figure 2A:
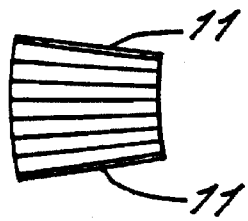
Figure 2B:
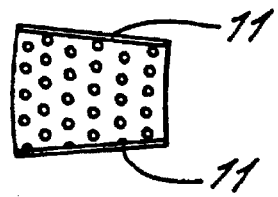

In the diagrammatic representation of an inhaler according to the invention shown in FIG. 1, the carrier disc 1 is rotatably mounted on the cylindrical pump body 2. The microstructures 3 are arranged in a circle on the underside of the carrier disc. The pump has a piston 4 with a pull rod 5 leading outside, ending in a knob 6. By means of the pull rod the piston can be pulled downwards counter to the pressure of a helical spring 7 and fixed in the tensioned state by means of a slide 8. In order to use the device for inhalation, the slide 8 is released by actuating the push button 9, so that the spring 7 presses the piston 4 upwards. This generates a blast of air which is guided through the nozzle 10 onto the powder accommodated between the microstructures. If the microstructures are rib-shaped the ribs are preferably aligned in the direction of the air current.

The apparatus described above for releasing a dose of active substance is expediently mounted in a housing which is fitted with a mouth tube and an air inlet. The air current is guided through the mouth tube, as the user breathes in, so that the quantity of powder released is mixed with the air breathed in.

There are numerous possible configurations for the inhaler. For example, in order to improve the coordination of the powder release with the act of breathing in, a mechanism may be incorporated by means of which the act of breathing in releases the barrier which holds the spring 7 in the tensioned state.

It is also possible first to blow the inhalation powder into a larger container with mouth tube and air inlet (e.g. according to German Utility Model G 8908273 or EP-A-79103369) and then to inhale through this device. In this way, the release of the powder for inhalation and the inhalation process can be kept apart from each other in time even more distinctly.

The provision of sectors containing active substance on a carrier disc is shown in FIG. 2. The individual sectors, each one of which contains one dose of active substance, are in this case separated from one another by partition walls. A mechanism (not shown here) ensures that the disc is moved on by one sector each time the device is actuated. The sectors (areas) shown in FIG. 2 have microstructures according to the invention (not shown in the drawings). FIG. 2*a* shows (on a larger scale) one of the areas in which the microstructure is made up of radial ribs (with a height of 100 μm, for example). FIG. 2*b* shows—again on a larger scale—the arrangement of bumps on such a field. Once again, the spacing between the bumps in a ring increases outwardly, in accordance with the larger circumference of the ring, the spacing from one ring to the next remaining substantially constant. The areas each having a dosage of active substance are separated from one another by partition walls 11.

Instead of being separated from one another by partition walls the individual doses of powder may also be separated by unfilled areas or may be passed through a mask which exposes only an area which is charged with precisely one dose of powder to the air blast from the nozzle 10. A preferred embodiment of this kind contains the carrier disc in a cassette so that all the other sectors are protected from contact. The section in which the dose of powder is to be released during use may also be closed off by a slide closure or some similar device so that the opening is not exposed until the carrier disc is placed in the inhaler.

It has been found that even a uniformly charged carrier can be used from which only part of the drug has been blown, because the dosage blown from a carrier of this kind shows a good degree of constancy.

The rotation of the carrier disc through one sector may, for example, be coupled to the tensioning of the spring 7 so that, on each tensioning, the carrier disc is rotated through one more sector. The carrier disc may be provided with means which ensure that the sectors are always in the correct position relative to the nozzle, e.g. by notches at suitable intervals and resilient members engaging therein.

We claim:

1. A powder inhaler device having a powder carrier comprising individual, elevated microstructures having a height of between about 10 and about 500 μm, said microstructures being arranged in a regular configuration in one or more sectors on a planar surface, wherein said microstructures define therebetween a contiguous surface onto which a powdered solid medicament can be deposited and from which said medicament can be released from each of said sectors individually.

2. The device according to claim 1, wherein the planar surface is selected from the group consisting of a belt, a plate and a disk.

3. The device according to claim 1, wherein the elevated microstructures are selected from the group consisting of cylindrical, bump-like, prismatic, conical, and frustoconical microstructures.

4. The device according to claim 1, wherein the elevated microstructures are selected from the group consisting of strips, ribs, pyramids and truncated pyramids.

5. The device according to claim 1, wherein the cross section of the elevated microstructures is selected from the group consisting of circular, elliptical and regular-polygonal cross-sections.

6. The device according to claim 1, wherein the elevated microstructures have a height between about 50 and 200 μm.

7. The device according to claim 1, wherein the contiguous surface of each sector is between about 4 and 50 $mm^2$.

8. A powder inhaler device comprising:

(a) a powder carrier in the form of a circular disc having a first side and a second side, said carrier being mounted for circular rotation about its center and having on its first side an annular array of sectors having elevated microstructures being between about 10 and about 500 μm in height, said elevated microstructures arranged in a regular configuration and forming therebetween a contiguous surface onto which a powdered solid medicament in the form of solid particles of respirable size can be deposited, each of said sectors containing a single dose of said powdered solid medicament;

(b) a cylindrical pump body having a first end and a second end;

(c) a piston housed within said cylindrical pump body being movable between said first end and said second end, whereby movement from said first end to said second end causes air to enter said cylindrical pump body through said first end while movement from said second end to said first end causes a blast of air to exit said cylindrical pump body through said first end;

(d) a helical spring for moving said piston within said cylindrical pump body;

(e) means for directing said blast of air into only one of said sectors, thereby causing said single dose of powdered solid medicament to be released from said carrier; and (f) a housing with a mouth tube through which said released single dose of powdered solid medicament can be inspired.

* * * * *